(12) United States Patent
Marzoli et al.

(10) Patent No.: US 6,361,204 B1
(45) Date of Patent: Mar. 26, 2002

(54) DEVICE FOR MEASURING THE THERMAL CONDUCTIVITY OF A FLUID

(75) Inventors: Cesare Marzoli, Lomagna; Giacinto Zilioli, Cernusco, both of (IT)

(73) Assignee: Thermoquest Italia S.p.A., Rodano (IT)

( * ) Notice: Subject to any disclaimer, the term of this patent is extended or adjusted under 35 U.S.C. 154(b) by 0 days.

(21) Appl. No.: 09/562,841

(22) Filed: May 1, 2000

(30) Foreign Application Priority Data

May 7, 1999 (IT) .......................................... MI99A0996

(51) Int. Cl.$^7$ .............................................. G01N 25/18
(52) U.S. Cl. ............................ 374/44; 374/10; 374/148
(58) Field of Search .............................. 374/43, 44, 10, 374/148

(56) References Cited

U.S. PATENT DOCUMENTS

| | | | |
|---|---|---|---|
| 2,751,777 A | | 6/1956 | Cherrier et al. |
| 3,075,377 A | * | 1/1963 | Lang ........................... 374/44 |
| 4,812,051 A | * | 3/1989 | Paulik et al. .................. 374/10 |
| 4,850,714 A | * | 7/1989 | Wiegleb ....................... 374/44 |
| 5,177,696 A | * | 1/1993 | Bonne .......................... 374/44 |
| 5,730,942 A | * | 3/1998 | Megerle et al. ............. 374/148 |
| 5,756,878 A | * | 5/1998 | Muto et al. .................... 374/44 |
| 5,772,321 A | * | 6/1998 | Rhodes ......................... 374/44 |

FOREIGN PATENT DOCUMENTS

| | | |
|---|---|---|
| DE | 2311103 A | 9/1974 |
| EP | 0382414 A | 8/1990 |
| EP | 0529295 A | 3/1993 |
| FR | 2456950 A | 12/1980 |
| GB | 1596648 A | 8/1981 |

\* cited by examiner

*Primary Examiner*—Diego Gutierrez
*Assistant Examiner*—Madeline Gonzalez
(74) *Attorney, Agent, or Firm*—Cobrin & Gittes

(57) ABSTRACT

A device for measuring the thermal conductivity of a fluid comprising a first detection section with at least one duct in which a gas flows and at least one heat sensitive resistance element placed in that duct, and a second detection section for the detection of an electrical resistance of the heat sensitive resistance elements. The device also comprises a thermoregulator to maintain the first detection section at a constant first temperature and a further thermoregulator to maintain at least part of the second detection section at a constant second temperature independent of the first temperature.

21 Claims, 2 Drawing Sheets

DEVICE FOR MEASURING THE THERMAL CONDUCTIVITY OF A FLUID

BACKGROUND OF THE INVENTION

FIELD OF THE INVENTION

The present invention relates to a device for measuring the thermal conductivity of a fluid, to be used in particular for the detection of compounds present in the same fluid.

The identification of the chemical composition of a substance raised to the gaseous or vapor state is usually done by gas chromatography. In such apparatus, a gaseous mixture, or a mixture of gas and vapor, containing the sample to be analyzed and an inert carrier gas, is made to flow, after an elution process, to a detector that measures variations in certain physical characteristics of the same gaseous mixture.

Devices that measure variation in the thermal conductivity of a fluid are widely used as substance analyzers in gas chromatography apparatus. Such devices detect variations in the conductivity of the gaseous mixture with which they are supplied, and give values that relate to the composition of the same gaseous mixture.

Detectors that measure the thermal conductivity of fluids consist schematically of a metal filament located inside a duct through which the gaseous mixture to be analyzed is made to flow. The metal filament, whose electrical resistance is temperature dependent, is heated by an electric current and the heat generated is transmitted to the inside walls of the duct mainly by conduction through the gaseous mixture.

Variations from one instant to the next in the thermal conductivity of the mixture—due to changes in the chemical composition of the same—cause variations in the flow of heat dissipated by the filament. Such variations in the heat flow lead to variations in the temperature of the filament, and accordingly, in its electrical resistance. The thermal conductivity of the gaseous mixture can be measured simply by measuring the electrical resistance of the metal filament as the gaseous mixture passes through the duct.

The practical implementation of such schemes, however, has encountered serious problems, such as drift in the voltage that controls the current of the metal filament and serious inaccuracies in the results when even small variations occur in the temperature of the mixture to be analyzed or in the temperature of the walls of the duct. A device of simple construction widely employed to overcome the aforementioned problems comprises an electrical measurement bridge (such as, for instance, a Wheatstone bridge) in which the two pairs of heat-sensitive resistance elements, diagonally opposed with respect to supply and detection, are placed in two respective ducts. Only carrier gas is made to flow in one of the ducts, while a mixture of carrier gas and sample to be analyzed is made to flow in the other, in such a way that the conductivity of the carrier gas alone constitutes the reference value to measure the conductivity of the carrier gas and sample mixture.

If the voltage across the terminals of the detector diagonal of the bridge when only carrier gas is made to flow in the duct is considered as the reference value, for instance, each variation of the voltage with respect to this reference value, observed in correspondence to the entry of the mixture to be analyzed into one of the ducts, will depend only on the nature and concentration of the substances present in the mixture.

In fact, any variation of the temperature of the carrier gas that occurs in both ducts, will not influence the detection. Nor will the latter be even affected by variations of the temperature of the ducts, since these, not being insulated thermally, are placed on a single support (defined below as the body of the detector) that is maintained at constant temperature.

One drawback not eliminated by similar embodiments is the short useful life of the resistance filaments placed in contact with the gas flow, due to their rapid oxidation and their contact with any corrosive compounds present in the gaseous mixture. The filaments need to be replaced frequently, but they are very expensive because of the requirement for characteristics of low reactivity and linearity of the voltage-temperature response. In particular, the known embodiment described above provides for frequent and simultaneous replacement of all four filaments.

Furthermore, the body of the detector, which supports two ducts and four filaments and must include a means of thermoregulation, is not very small and permits neither convenient use in reduced spaces nor the support to be held at constant temperature.

SUMMARY OF THE INVENTION

The device according to the invention comprises a first section with at least one duct for the passage of a fluid whose thermal conductivity is to be measured and at least one heat-sensitive resistance element placed within that duct, and a second section for the detection of an electrical quantity which is dependent on the heat-sensitive resistance element. There are first means of thermoregulation to maintain the first section at a constant temperature T1, and second means of thermoregulation to maintain the second section at a constant temperature T2 independent of the temperature T1 of the first section. According to a preferred embodiment of the invention, the device comprises a first section having two ducts in which there are located respectively two heat-sensitive resistance elements and a second section that forms an electrical measurement bridge with the resistance elements present in the first section. The fluid whose thermal conductivity is to be measured and a reference fluid respectively are made to flow in the two ducts. Furthermore, the two sections are maintained at independent temperatures T1 and T2 by their respective means of thermoregulation.

A preferred embodiment of the invention will be described by way of example and not of limitation, with reference to the figures attached, in which:

DESCRIPTION OF THE PREFERRED EMBODIMENTS

Figure 1:
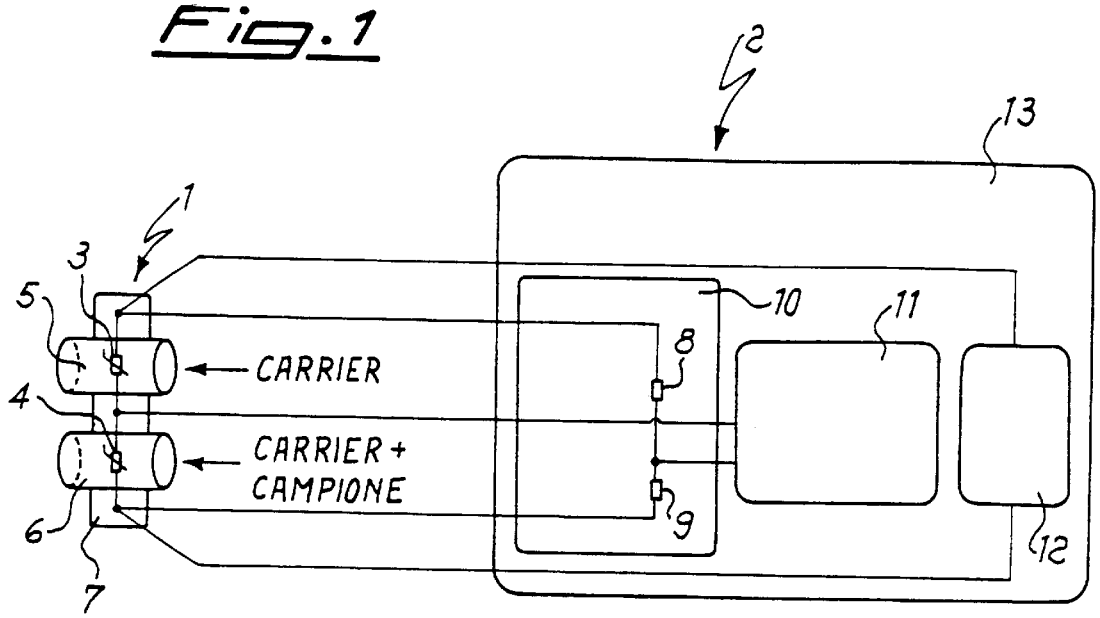
FIG. 1 is a schematic representation of a preferred embodiment of the device according to the invention.
Figure 2:
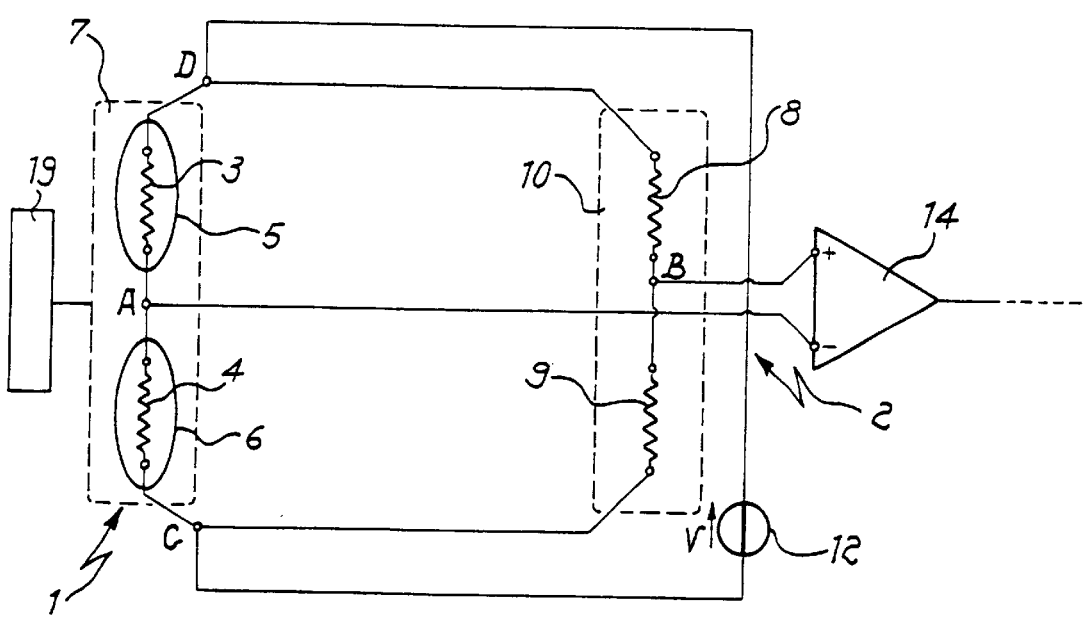
FIG. 2 is a partial electrical circuit of the device of FIG. 1.

With reference to FIGS. 1 and 2, the preferred embodiment of the device for measuring the thermal conductivity of a fluid according to the invention comprises a first section 1—which forms the body of the detector—and a second section 2, which are electrically connected. The first section 1 comprises a support 7 that is maintained at a temperature T1 by first means of thermoregulation (19) (FIG. 2). On the support 7 are arranged two ducts 5 and 6 for the passage respectively of a reference fluid and of a fluid whose thermal conductivity is to be measured. In use with gas chromatography apparatus, in particular, the reference fluid is a carrier gas, while the fluid whose thermal conductivity is to be measured consists of a mixture of carrier gas and of a sample in the gaseous state.

Furthermore, two heat-sensitive resistance elements 3 and 4 (for brevity defined in succession by the term filaments) are placed within the ducts 5 and 6, whose electrical resistance changes proportionally with the temperature they assume.

The second section 2 of the device comprises a support 10 having two resistance elements 8 and 9, an element 11 to detect an electrical quantity, of which the (differential) amplifier 14 of FIG. 2 is part, and a power supply 12. In particular, the support 10 is endowed with means of thermoregulation 16, 17 and 18 (shown in FIG. 4) to maintain the support 10 at a temperature T2 independent of the temperature T1 of the first section 1.

The filaments 3 and 4, the resistance elements 8 and 9, the power supply 12 connected to the terminals C and D and the detection element 11, connected to the terminals A and B, are interconnected to form an electrical measurement bridge.

If the detection element 11 is such as to measure the voltage difference of the bridge with respect to the terminals A and B, then the reference value could be set as zero for that voltage of the bridge when no fluid is flowing within the ducts, or when only the carrier gas is flowing in both the ducts. Each deviation of the voltage with respect to the zero value will therefore be dependent on the variation of thermal conductivity of the fluid to be measured with respect to the thermal conductivity of the reference fluid, provided that the temperature of the ducts 5 and 6 is maintained constant and that the characteristics of the filaments are identical.

However, variations in the temperature of the resistance elements 8 and 9 could influence the detection of variations in the voltage across. terminals A and B. In fact, even limited variations of the temperature of the surrounding environment could modify the resistance of the elements 8 and 9 and lead to undesirable unbalance of the electrical measurement bridge.

Maintaining the resistance elements 8 and 9 at a temperature T2 superior to the temperature of the surrounding environment in a such way that any change in the external temperature does not influence the thermal conditions of the elements 8 and 9, thus prevents variations of the voltage across the terminals A and B dependent on the elements 8 and 9. Note however that temperature T2 is different from and very much lower than temperature T1.

Figure 3:
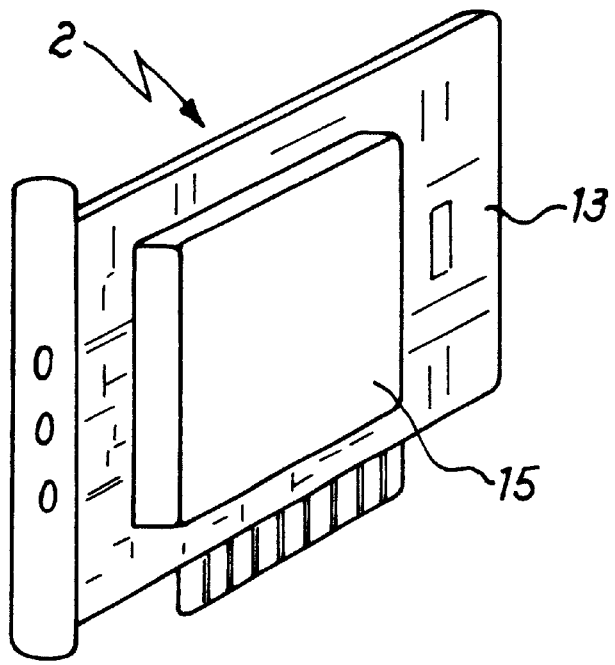
FIG. 3 is a perspective view of the second section of the preferred embodiment of the device according to the invention.
Figure 4:
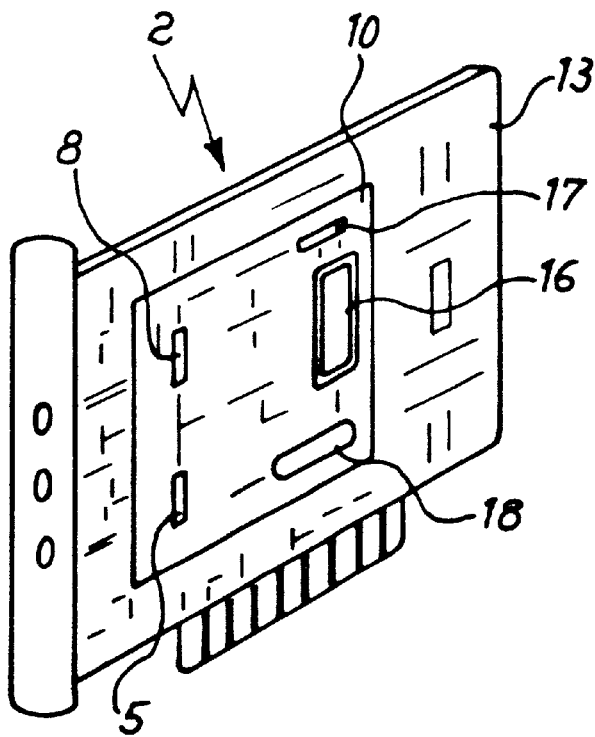
FIG. 4 is a schematic perspective view of the second section of FIG. 3, in which the protective shell has been removed.

The characteristic elements of the second section 2 can be integrated on a board 13 that could comprise circuits and electronic components to permit to interface with a computer (see FIGS. 3 and 4).

The board 13 comprises the support 10, that could be the alumina of a hybrid circuit, on which are mounted the resistance elements 8 and 9. The support 10 is maintained at temperature T2 by thermoregulation means and is placed under a shell 15 that could also be insulated if necessary. The means of thermoregulation of the support 10 could comprise a probe to measure the local temperature 17, an automatic controller 16 and a heating element 18, the latter being preferably produced with MOS technology. Such means of thermoregulation of the support 10 are low-cost miniaturized components that are easily obtained on the market.

The use of only two filaments 3 and 4 in the fluid flow brings a reduction of the replacement costs of the same filaments and a limitation of the associated costs of the electrical power used by the device when compared to embodiments with four filaments. In fact, the means of thermoregulation in the second section use less electrical power, because of the reduced dimensions of the section to be heated, and the presence of only two filaments halves the requirement of electrical current for their heating.

The reduced dimensions of the first section 1, furthermore, favor its employment in limited spaces.

What is claimed is:

1. A device for measuring thermal conductivity of a fluid, of the type comprising at least one duct in which said fluid flows and at least one heat-sensitive resistance element placed in said duct, and electrical components for the detection of an electrical quantity dependent on variations of the electrical resistance of the heat-sensitive resistance element(s) located in said duct(s), characterized in that said at least one duct forms a first section heated by first means of thermoregulation to maintain said first section of detection at a first constant temperature (T1), and said electrical components form a second section heated by second means of thermoregulation to maintain at least part of said second section at a second temperature (T2) independent of said first temperature (T1), and in that said electrical components are connected to said heat-sensitive resistance element(s) in an electrical measurement bridge.

2. A device for measuring the thermal conductivity of a fluid according to claim 1, characterized by said second section comprising electrical components connected to said at least one heat-sensitive resistance element in an electrical measurement bridge.

3. A device for measuring the thermal conductivity of a fluid according to claim 2, characterized by said electrical components of said second section comprising at least two resistance elements.

4. A device for measuring the thermal conductivity of a fluid according to claim 1, characterized by said first section comprising a first duct in which said fluid flows, at least one first heat-sensitive resistance element placed in said first duct, a second duct in which a reference fluid flows and at least one second heat-sensitive resistance element placed in said second duct.

5. A device for measuring the thermal conductivity of a fluid according to claim 4, characterized by said second section comprising electrical components connected to said first and second heat-sensitive resistance elements in an electrical measurement bridge.

6. A device for measuring the thermal conductivity of a fluid according to claim 5, characterized by said electrical components of said second section comprising at least two resistance elements.

7. A device for measuring the thermal conductivity of a fluid according to claim 1, characterized by said first section and said second section respectively being arranged on different supports.

8. A device for measuring the thermal conductivity of a fluid according to claim 1, characterized by said second section and said second means of thermoregulation being arranged on a removable board.

9. A device for measuring the thermal conductivity of a fluid according to claim 1, characterized by at least part of said second section and said second means of thermoregulation being placed in a shell which is sealed with respect to the external environment.

10. A device for measuring the thermal conductivity of a fluid according to claim 9, characterized by said shell comprising a covering in thermal insulating material.

11. A device for measuring the thermal conductivity of a fluid according to claim 1, characterized by said second means of thermoregulation comprising at least one heating element produced by MOS technology.

12. A device for measuring the thermal conductivity of a fluid according to claim 1, characterized by said second temperature (T2) being higher than the external environmental temperature and different from said first temperature (T1).

13. A device for measuring the thermal conductivity of a fluid according to claim 1, characterized by said second temperature (T2) being lower than said first temperature (T1).

14. A device for measuring the thermal conductivity of a fluid according to claim 4 in combination with said fluid whose thermal conductivity is to be measured, said fluid arranged to flow within said first duct and being a mixture composed of a carrier gas and one or more substances in the vapor state and, in further combination with said reference fluid flowing in said second duct and consisting of said carrier gas.

15. Apparatus for analysis of a chemical composition of substances by means of gas chromatography, characterized by comprising at least one device for measuring the thermal conductivity of a fluid according to claim 1.

16. Method for measuring the thermal conductivity of a fluid, in which said fluid flows in a duct of a first section in which there is a heat-sensitive resistance element and in which an electrical quantity dependent on variations in the electrical resistance of said heat-sensitive resistance element is detected in a second section, characterized by said first section being maintained at a first temperature (T1) and said second section being maintained at a second temperature (T2) independent of said first temperature (T1).

17. A method for measuring the thermal conductivity of a fluid according to claim 16, characterized by a reference fluid flowing in a second duct of said first section in which there is a heat-sensitive resistance element.

18. A method for measuring the thermal conductivity of a fluid according to claim 17, characterized by said fluid whose thermal conductivity is to be measured being a mixture composed of a carrier gas and of one or more substances in the gaseous state and said reference fluid consisting of said carrier gas.

19. A method for measuring the thermal conductivity of a fluid according to claim 16, characterized by said second temperature (T2) being higher than the external environment temperature and different from said first temperature (T1).

20. A method for measuring the thermal conductivity of a fluid according to claim 16, characterized by said second temperature (T2) being lower than said first temperature (T1).

21. A device to measure thermal conductivity of a fluid, comprising:
  a detection section having at least one duct;
  a thermoregulator configured and arranged to maintain the detection section at a first constant temperature (T1);
  at least one heat-sensitive resistance element within said duct;
  a further detection section;
  a detector of an electrical quality dependent on variations of electrical resistance element, the detector being within the further detection section; and
  a further thermoregulator to maintain at least a part of the further detection section at a second temperature (T2) that is independent of the first temperature (T1).

* * * * *